(12) United States Patent
Fitzgerald (10) Patent No.: US 7,270,649 B2
(45) Date of Patent: Sep. 18, 2007

(54) INTRAVENOUS CATHETER DEVICE

(75) Inventor: Lisa M. Fitzgerald, Sarasota, FL (US)

(73) Assignee: P. Rowan Smith, Jr., Houston, TX (US)

( * ) Notice: Subject to any disclaimer, the term of this patent is extended or adjusted under 35 U.S.C. 154(b) by 306 days.

(21) Appl. No.: 10/890,645

(22) Filed: Jul. 14, 2004

(65) Prior Publication Data

US 2006/0015071 A1    Jan. 19, 2006

(51) Int. Cl.
*A61M 5/178* (2006.01)

(52) U.S. Cl. .............................. 604/164.01; 604/168.01

(58) Field of Classification Search ............. 604/93.01, 604/6.16, 164.01, 167.05, 168.01, 167.01, 604/535, 164.08, 263, 164.09, 533, 115, 116, 604/110; 128/DIG. 26
See application file for complete search history.

(56) References Cited

U.S. PATENT DOCUMENTS

| 5,246,426 | A | * | 9/1993 | Lewis et al. | ............ 604/168.01 |
| 5,312,359 | A | * | 5/1994 | Wallace | .................. 604/164.08 |
| 5,704,914 | A | * | 1/1998 | Stocking et al. | ........ 604/164.07 |
| 7,052,483 | B2 | * | 5/2006 | Wojcik | ........................ 604/162 |

* cited by examiner

*Primary Examiner*—Matthew DeSanto
(74) *Attorney, Agent, or Firm*—Richard L. Moseley (57) ABSTRACT

A catheter appliance having a catheter in fluid communication with a luer connector is releasably secured to a catheter applicator having a track for slidably mounting a needle carrier module. The needle carrier module includes a hypodermic which extends through the catheter for insertion and which is in fluid communication with a flashback indicator on the module. The catheter applicator includes a needle cavity for containing the hypodermic needle after use.

5 Claims, 7 Drawing Sheets

INTRAVENOUS CATHETER DEVICE

BACKGROUND OF THE INVENTION

1. Field of the Invention

The present invention relates to a device for the insertion of a flexible catheter into a vein of a patient for intravenous administration of fluids. More Particularly the invention relates to devices wherein the flexible catheter is inserted into the vein by sharp needle about which the catheter is snugly mounted, and the needle and catheter are inserted into the vein and the needle retracted leaving the catheter in place. More particularly the invention relates to a catheter insertion device wherein the insertion needle is retractable into the device after removal. Most particularly the invention relates to a catheter insertion device having a "flashback" detector and a built-in sharps container for needle safety after the application is complete.

2. Related Art

The development of flexible intravenous catheters has greatly increased the comfort of patients during intravenous administration of medicinal fluids. The flexible catheter prevents unwanted puncture of the vein. The flexible catheter normally consists of a narrow tube of NYLON or TEFLON construction with a rigid member attached at the rear end for connection to the source of fluid to be administered.

Because the catheter is flexible it cannot by itself be inserted into the vein. Therefore, the catheter is snugly nested about a sharp hypodermic type needle which can be inserted into the vein. After insertion the sharp needle is withdrawn leaving the catheter in place for connection to the fluid source. The insertion needle is usually discarded as it is intended for a single use only. Often the needle is discarded in a careless manner leaving the exposed needle point as a hazard.

Accidental needle prick has been a problem for years in the health care industry. However, the advent of the HIV or AIDS virus has focused attention on the problem. While several diseases, such as viral hepatitis, may be contracted from bodily fluids of infected persons, HIV has caused the most concern because to date no preventative or cure is known. Protection against accidental needle prick is expected to remain a concern even after a vaccine or cure is found, an ounce of prevention being worth a pound of cure.

Earlier U.S. Pat. Nos. 5,019,019 and 5,176,650 have addressed this problem in regard to catheter insertion devices.

SUMMARY OF THE INVENTION

To protect against accidental needle prick a catheter and insertion device are provided wherein the needle is retractable within the device after insertion of the catheter. The device comprises basically a catheter applicator, a catheter appliance releasably secured to the applicator and a needle carrier module slidably mounted on the applicator. The device may be configured with either a one-way check valve for use as an infusion port or a check valve opened by the insertion of a male luer connector for use as a blood draw port. The device has a paddle applicator that includes a "flashback" indicator and a built-in sharps container for needle safety after the application is complete. The paddle assembly, containing the needle and flashback indicator, is removed and discarded after the catheter appliance is secured. The device completely protects the administrator from blood products and sharps during all phases of the application.

DESCRIPTION OF THE PREFERRED EMBODIMENTS

For a detailed description of the preferred embodiment the reader is referred to the appended figures in which like components are given like numerals for ease of reference.

Figure 4:
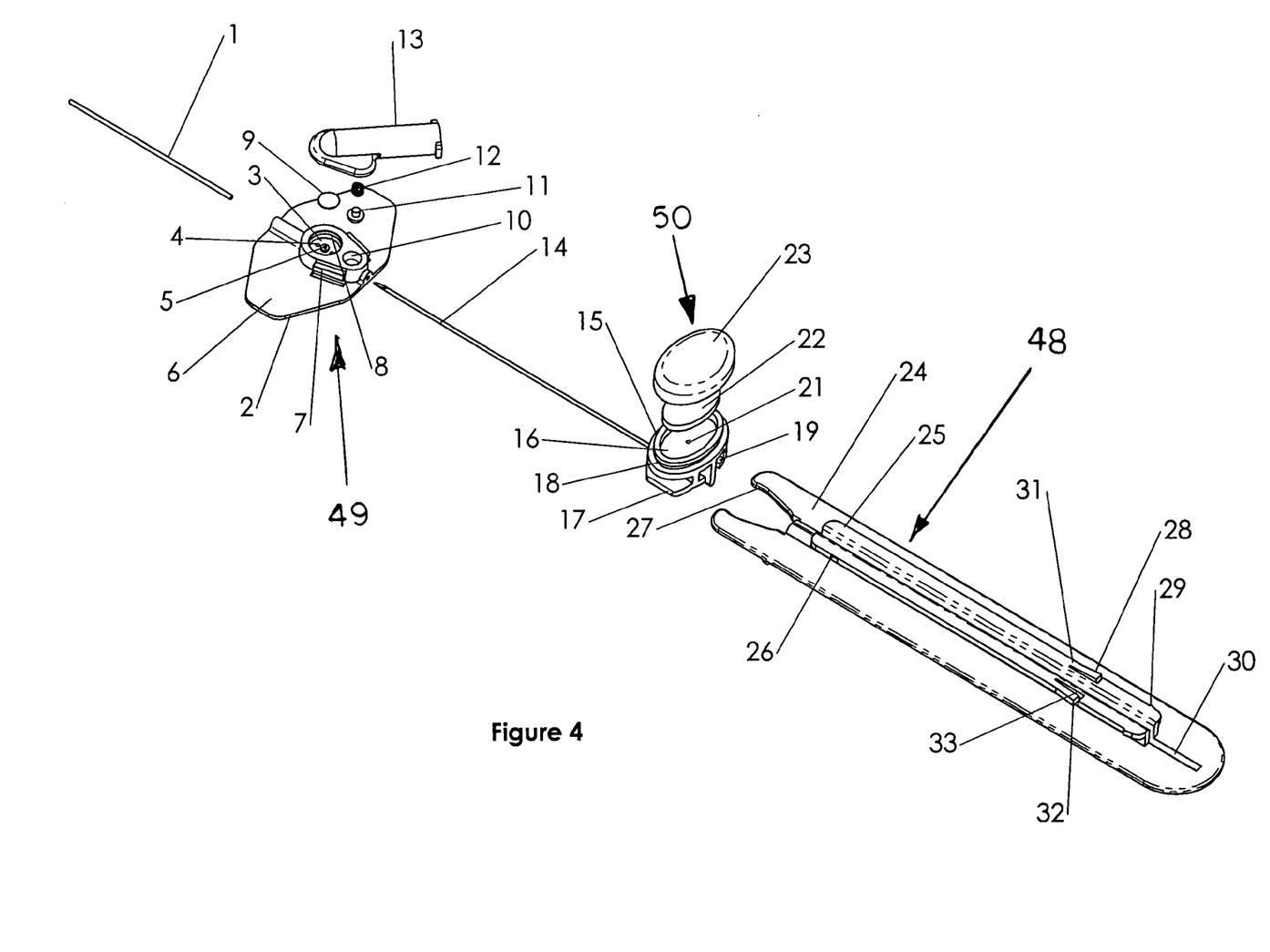
FIG. 4 is an exploded view of the embodiment shown in FIG. 1.

Referring first to FIG. 4, an exploded view of a preferred embodiment, the catheter insertion device is seen to comprise three discreet sections—a catheter applicator generally indicated at 48; a catheter appliance generally indicated at 49 and a needle carrier module generally indicated at 50.

The catheter applicator 49 is comprised of paddle 24 having a track 25 down the center with a catheter retainer pawl 27 at one end and a needle cavity 30 at the opposite end. Also near the end of the track are a rear track stop 29 with needle carrier lock pawl 28 having retaining surface 32 and bending section 31 which may deflect into tab relief slot 33. A forward retaining notch 26 is located near the front of the track 25 adjacent the pawl 27.

The catheter appliance itself 49 is comprised of catheter 1 secured in catheter carrier body 2 which includes a catheter carrier flap 6. Paddle retainer 7 aids in the connection of the catheter appliance 49 to catheter applicator 48. A luer connector 13 is fitted into luer connector recess 8 and held in place by luer retaining ring 3. The luer 13 may be fixed in position or rotatable within the recess 8. Fluid flow aperture 4 allows flow between catheter 1 and luer connection 13. A valve membrane 9 is retained over the flow aperture by valve retainer 5. A plunger cavity 10 is located rear of the luer connection which contains plunger seal 11 and plunger seal spring 12.

The Needle carrier module 50 is comprised of hypodermic needle 14 secured to needle carrier 15. The hypodermic needle 14 is in fluid communication with flashback cavity 16 by flashback aperture 21. The flashback indicator 22 can be observed through the transparent flashback cap 23 which is held in place in cap retainer recess 18. The needle carrier 50 rides in track 25 on track follower 19. Needle carrier spring 17 retains the needle carrier in track 25.

Figure 1:
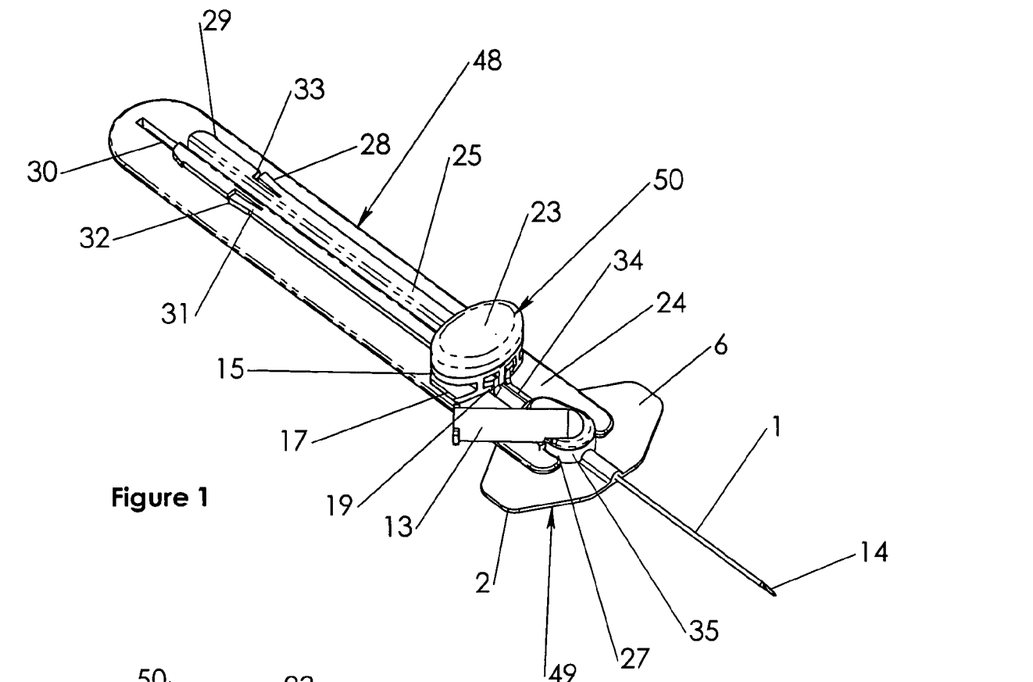
FIG. 1 shows one embodiment of the device ready for insertion into a vein with the hypodermic needle and catheter fully exposed.
Figure 2:
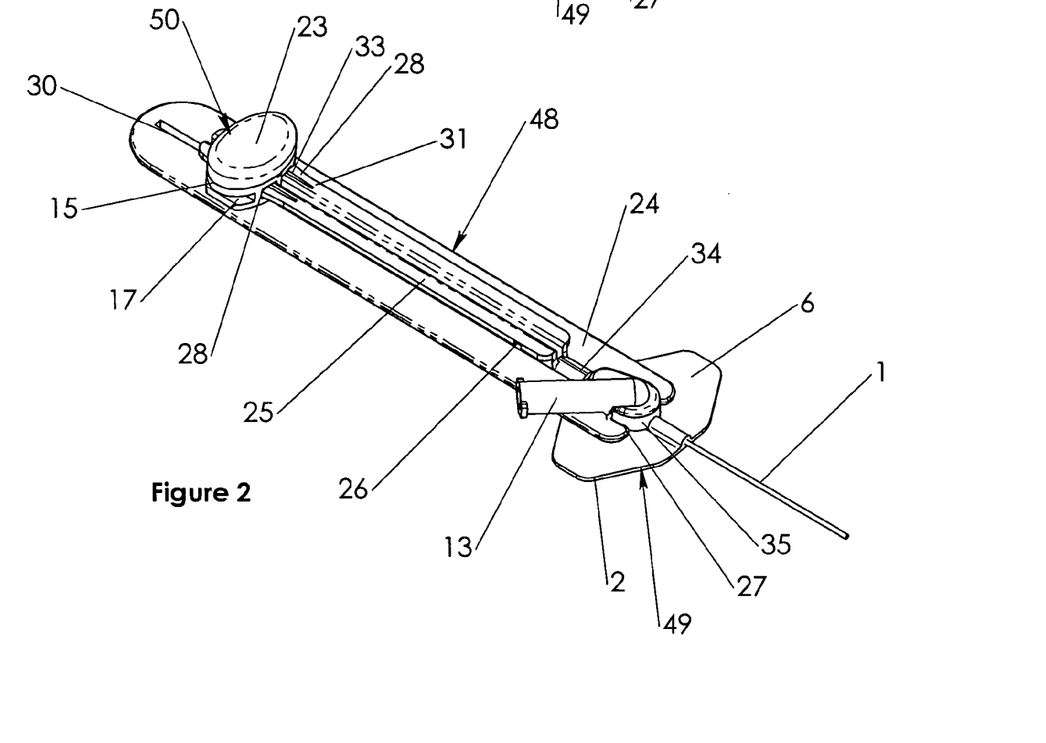
FIG. 2 shows the device of FIG. 1 in the fully retracted position.
Figures 5, 6, 6A, 7:
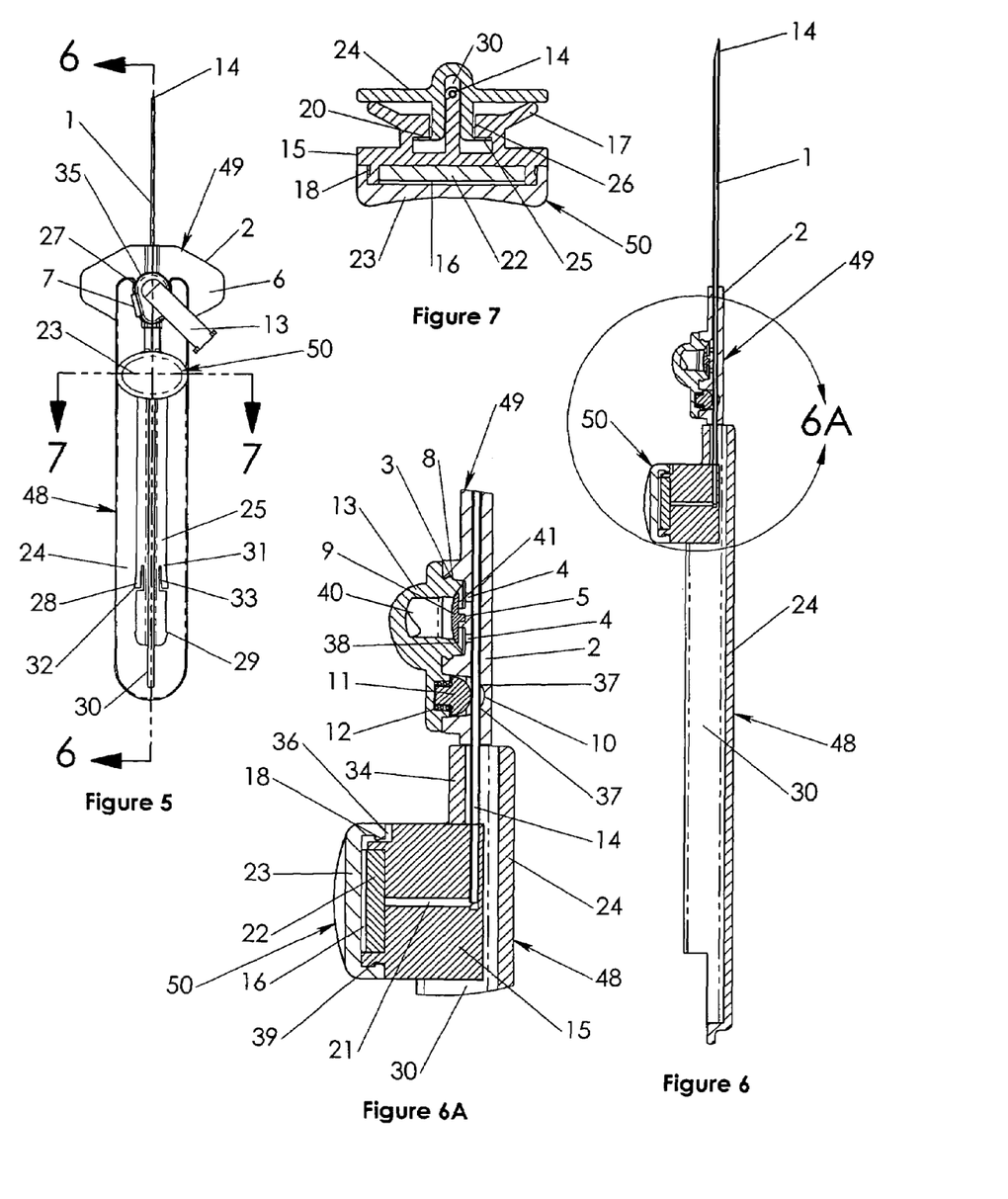
FIG. 5 is a top plan view of the device of FIG. 1 with the catheter and needle ready for insertion into a vein with the hypodermic needle and catheter fully exposed.
FIG. 6 is a cross sectional view taken along line 6-6 of FIG. 5.
FIG. 6A is an enlarged cross sectional view of the area circled in FIG. 6.
FIG. 7 is a cross sectional view taken along line 7-7 of FIG. 5.

Referring now to FIGS. 1, 6A and 7, the device is shown in the initial state with the catheter applicator 48 and the catheter appliance 49 held together by a light snap fit comprised of the two catheter retainer pawls 27, held in position by the elastic property of paddle 24 around the catheter retainer surface 35. Referring also to FIG. 4, the paddle 24 is held in the axial position on the proximal side by paddle retainer 7 and on the distal side by the catheter carrier flap 6, symmetrical on the mid-plane. The needle carrier module 50 comprised of needle carrier 15, hypodermic needle 14, flashback indicator 22 and flashback indicator 22 and flashback cap 23 is locked in position by retainer pawl 20 on the needle carrier 15 by engaging the forward retainer notch 26 on the under side of track 25, biased by the needle carrier spring 17. The carrier module 50 is also retained by track follower 19 on the under side of track 25. The luer connector 13 is secured and sealed to the catheter carrier body 2 by means of the luer connector retainer ring 3, located on luer connector 13, snapping into the luer connector recess 8, located in the catheter carrier body 2. Hypodermic needle 14 protrudes out the distal end of the catheter 1 and is ready for a percutaneous insertion.

Referring to FIGS. 1,4,5,6 and 6A, during use a "flashback" or indication of the positioning, of the catheter 1 in the vein is indicated when blood expelled through the hypodermic needle 14 and flashback aperture 21 is absorbed by a porous material, the flashback indicator 22. The flashback indicator 22 is located in the flashback cavity 16 and retained by a transparent flashback cap 23. The flashback cap 23 is secured to the needle carrier by the cap retainer barb 39, located on the flashback cap 23, engaging the cap retainer recess 18 on the needle carrier 15. A flashback vent 36 is molded into the needle carrier 15 to keep the internal volume of the flashback cavity 16 at atmospheric pressure, allowing blood to flow at typical venous pressures to the flashback indicator 22. Any blood present in the flashback indicator 22 can viewed through the transparent flashback cap 23.

After the catheter has been successfully inserted the hypodermic needle 14 is moved to the needle-safe position as best seen in FIGS. 2,4,7,9A and 10. To achieve, this pressure is applied to the transparent flashback cap 23, deforming the needle carrier spring 17 located on needle carrier 15, allowing the retainer pawl 20 to disengage from forward retainer notch 26. This allows the needle carrier module 50 to freely slide longitudinally along the track 25 to a position retained by reartrack stop 29 at the distal end of track 25. Carrier module 50 is also impeded from forward motion needle carrier lock pawl 28. Needle carrier lock pawl 28 captures the needle carrier module 50 by deflecting inward, and as relieved by tab relief slot 33, to accommodate the inner volume of needle carrier 15 as needle carrier 15 slides along and is confined by track 25. After the needle carrier module 50 passes, the return deflection force of carrier lock pawl 28 is applied by the distortion strain of the cross section geometry, at the bending section 31, to a normal as molded condition. This returns the retaining surface 32 of carrier lock pawl to a position blocking needle carrier 15, thereby locking the needle carrier module 50 on track 25. In this position the hypodermic needle 14 in the needle cavity 30 with the needle tip further protected by needle tip guard 34.

The operation of the plunger seal 11 and valve membrane 9 are best illustrated with reference first to FIGS. 1,4-6 and 6A. When the hypodermic needle 14 is in place through needle aperture 37 in the catheter carrier body 2 and catheter 1 the bias of the seal spring 12 holds the plunger seal 11 against hypodermic needle 14. Referring now to FIGS. 2,4,8,9 and 9A, as the hypodermic needle 14 is retracted into the catheter applicator 48, the plunger seal 11, biased by the plunger seal spring 12, drops into the plunger cavity 10, sealing the apertures formed by the intersection of needle aperture 37 and plunger cavity 10. This seal prevents fluid backflow toward the proximal end of catheter appliance 49.

Figures 8, 9, 9A, 10:
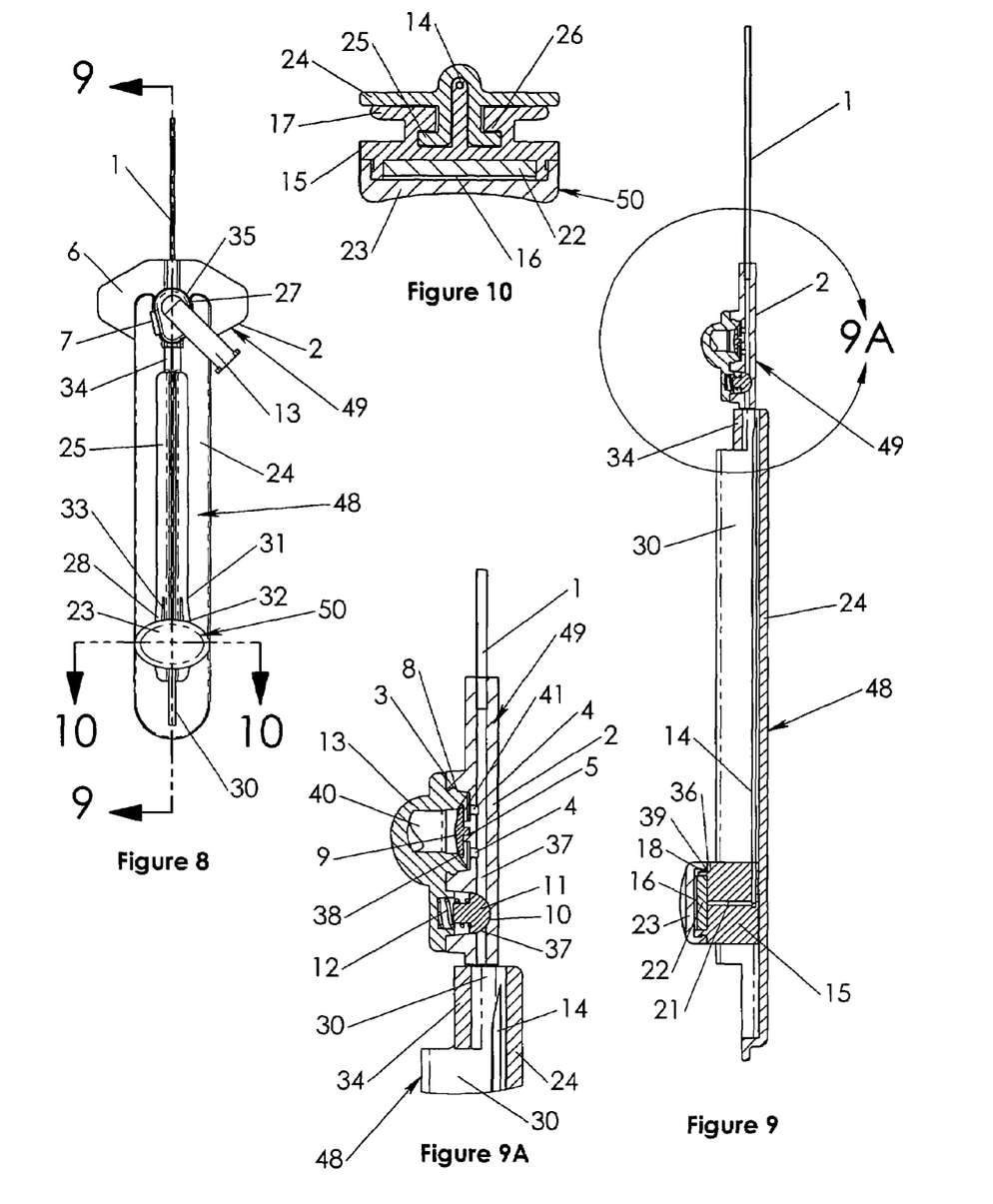
FIG. 8 is top plan view of the device of FIG. 1 with the needle in the retracted position.
FIG. 9 is a cross sectional view of the device taken along line 9-9 of FIG. 8.
FIG. 9A is an enlarged cross sectional view of the area circled in FIG. 9.
FIG. 10 is a cross sectional view of the device taken along line 10-10 of FIG. 8.
Figure 11:
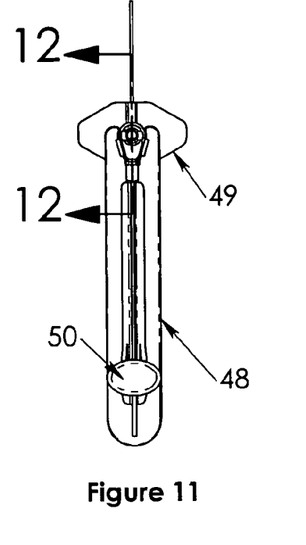
FIG. 11 is a top plan view of a second embodiment the device with the needle in the retracted position.
Figure 12:
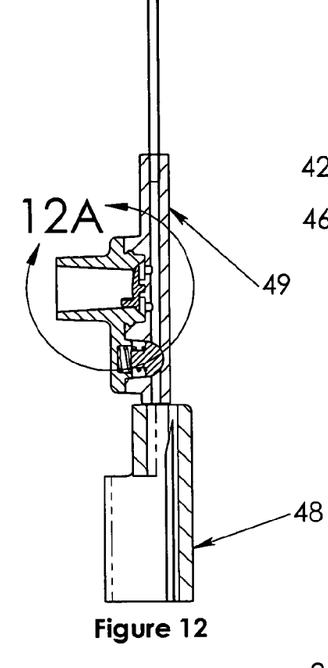
FIG. 12 is a cross sectional view of the device taken along line 12-12 of FIG. 11.
Figure 12A:
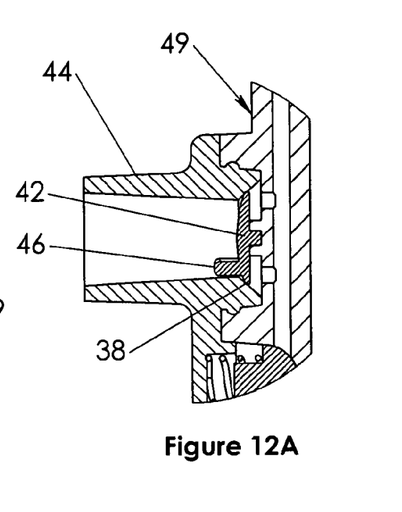
FIG. 12A is an enlarged cross sectional view of the area circled in FIG. 12.
Figure 13:
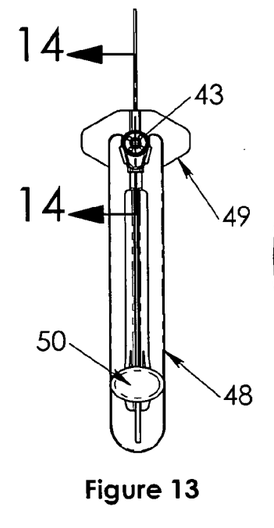
FIG. 13 is a top plan view of a third embodiment of the device with the catheter in the exposed position with the needle in the retracted position.
Figure 14:
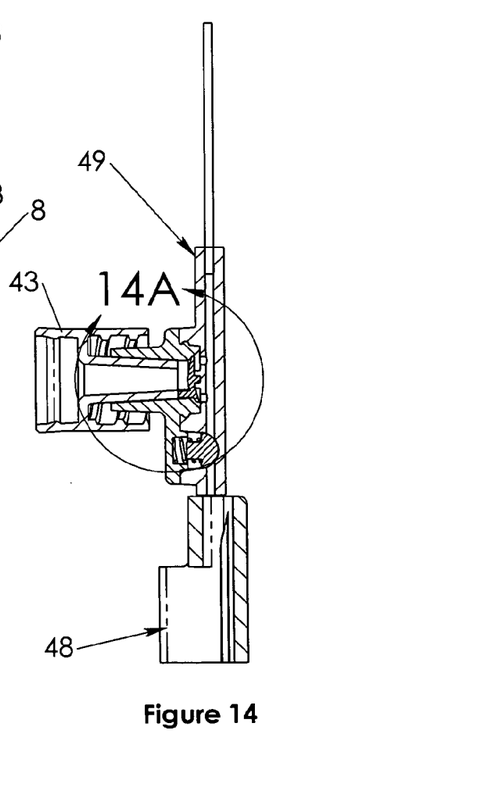
FIG. 14 is a cross sectional view of the device taken along line 14-14 in FIG. 13.
Figure 14A:
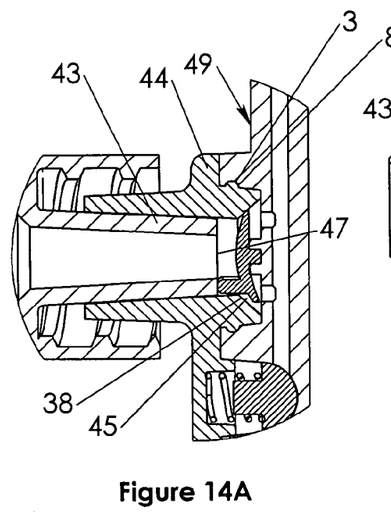
FIG. 14A is an enlarged cross sectional of the area circle in FIG. 14.
Figure 15:
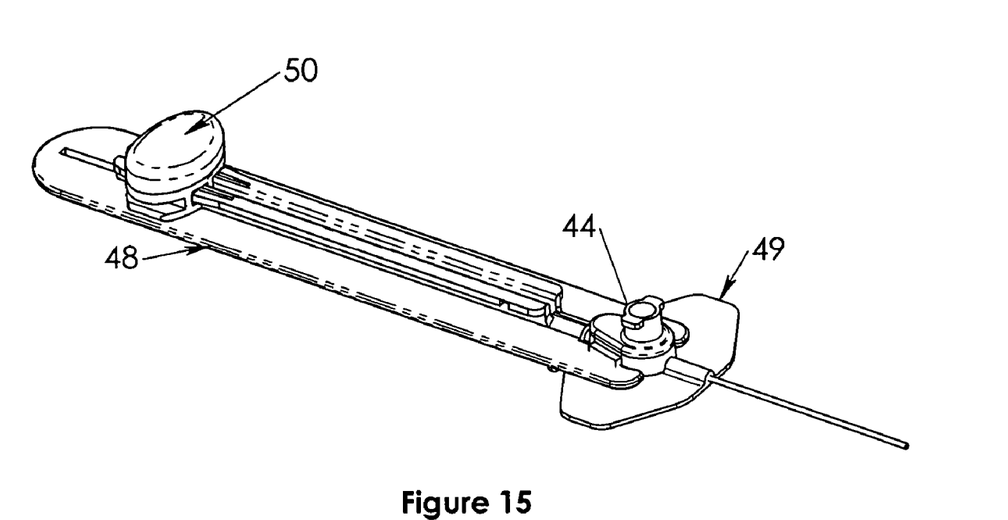
FIG. 15 is an isometric view of the either of the embodiments shown in either FIG. 12 or 13.

With the hypodermic needle 14 retracted and the plunger seal 11 fully engaged, fluid will flow through the luer connector 13 and to the check valve comprised of valve membrane 9 pressing against sealing surface 38 in the luer connector inner cavity 40. The valve membrane 9 is held concentric to the luer connector inner cavity 40 by the valve retainer 5, capturing a tab centered on the valve membrane 9. As the pressure in the connector inner cavity 40 increases, the elastic property of the valve membrane 9 allows the seal to deform and break contact at the sealing surface 38, thereby allowing fluid flow through the luer connector 13, fluid flow aperture 4, needle aperture 37 and catheter 1 into the vein. Any back pressure applied to valve face 41 on valve membrane 9 further compresses valve membrane 9 against sealing surface 38 and increases the integrity of the seal.

Figure 3:
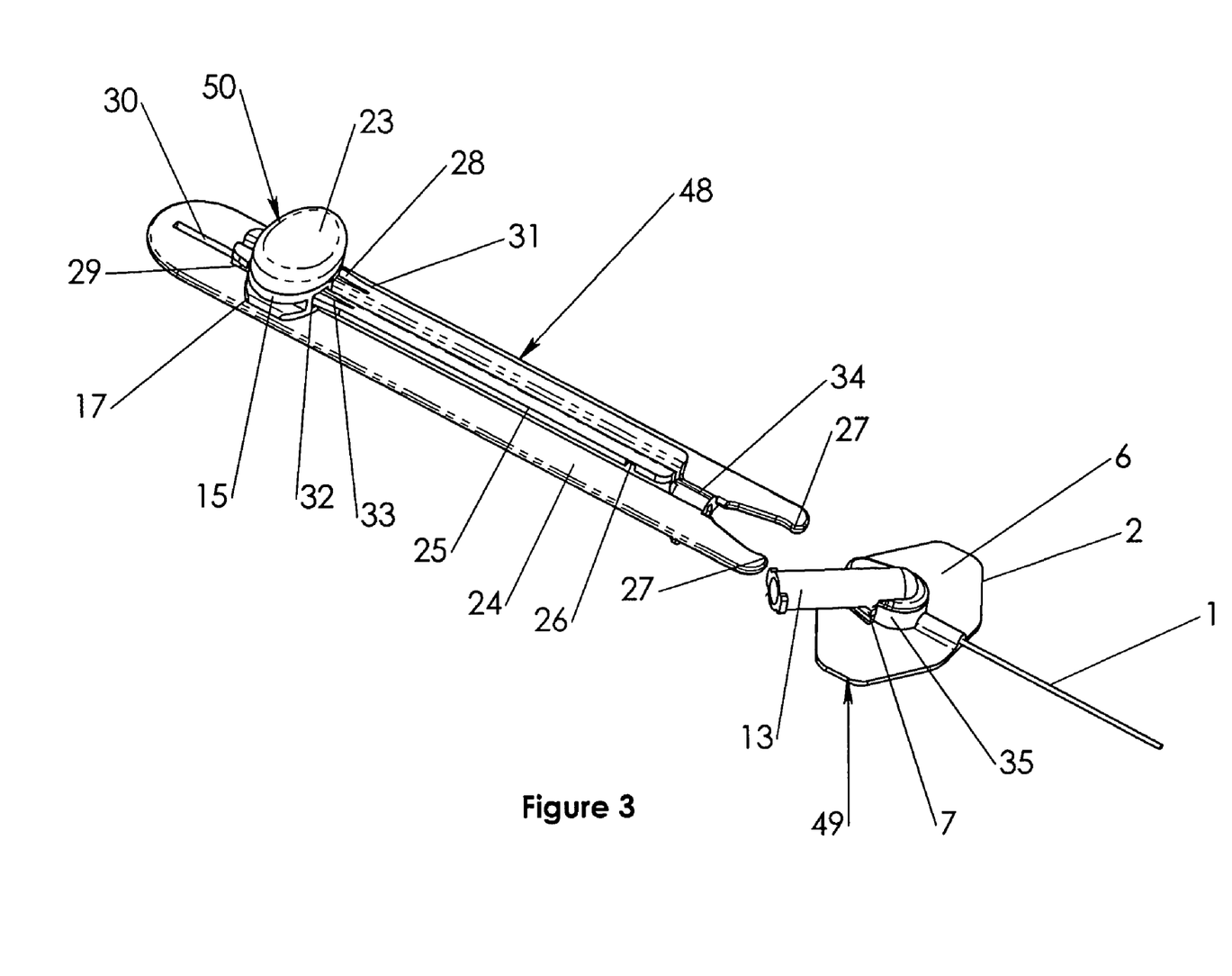
FIG. 3 shows the device of FIG. 1 with the catheter applicator separated from the catheter.

Referring to FIG. 3, after the catheter 1 is placed in a vein and the catheter appliance 49 secure to the skin, the applicator 48 along with the needle carrier module 50 is unsnapped from the catheter appliance 49 and discarded. Catheter carrier flap 6 is used as an attachment surface to secure the catheter appliance 49 to the patient.

In a second embodiment the device may be used as a blood draw port. This embodiment is particularly shown in FIGS. 11,12,12A,13,14,14A and 15. A vertical luer 44 is secured and sealed to the catheter carrier body 2 by means of the luer retainer ring 3, located on luer connector 13, snapping into the luer connector recess 8, located in the catheter carrier body 2. A standard male luer connector 43 is screwed onto the vertical luer connector 44. The luer body 47 on standard male luer connector 43 applies pressure to valve actuator 46, on two-way valve membrane 42, deforming the two-way valve membrane 42 at sealing surface 38. A flow path 45 is opened and blood can be drawn from the vein.

The foregoing description of the invention has been directed to a particular preferred embodiment of the present invention for the purposes of explanation and illustration. It will be apparent to those skilled in the art that many modifications and changes in the apparatus may be made without departing from the scope and spirit of the invention. It is therefore intended that the following claims cover all equivalent modifications and variations as fall within the scope of the invention as defined by the claims.

For quick reference all of the reference numerals are listed in Table I below and their corresponding parts identified with the figures in which the parts are identified. The parts may be shown in other figures but are identified by the reference numerals in the listed figures only.

TABLE I

| | | |
|---|---|---|
| 1 | Catheter | 1-6, 8-9, 9A |
| 2 | Catheter carrier body | 1-6, 6A, 8-9, 9A |
| 3 | Luer connector retainer ring | 4, 6A, 9A, 14A |
| 4 | Fluid flow aperture | 4, 6A, 9A |
| 5 | Valve retainer | 4, 6A, 9A |
| 6 | Catheter carrier flap | 1-5, 8 |
| 7 | Paddle retainer | 3-5, 8 |
| 8 | Luer connector recess | 4, 6A, 9A, 14A |
| 9 | Valve membrane | 4, 6A, 9A |
| 10 | Plunger cavity | 4, 6A, 9A |
| 11 | Plunger seal | 4, 6A, 9A |
| 12 | Plunger seal spring | 6A, 9A |
| 13 | Luer connector | 1-5, 8, 9A |
| 14 | Hypodermic needle | 1, 4-6, 6A, 7, 9, 9A, 10 |
| 15 | Needle carrier | 1-4, 6A, 7, 10 |
| 16 | Flashback cavity | 4, 6A, 7, 9-10 |
| 17 | Needle carrier spring | 1-4, 7, 10 |
| 18 | Cap retainer recess | 4, 6A, 7, 9 |
| 19 | Track follower | 1, 4 |
| 20 | Retainer pawl | 7 |
| 21 | Flashback aperture | 4, 6A, 9 |
| 22 | Flashback indicator | 4, 6A, 7, 9, 10 |
| 23 | Transparent flashback cap | 1-5, 6A, 7-9, 10 |
| 24 | Paddle | 1-6, 6A, 8-9, 9A, 10 |
| 25 | Track | 1-5, 7-8, 10 |
| 26 | Forward retainer notch | 2-4, 7, 10 |
| 27 | Catheter retainer pawl | 1-5, 8 |
| 28 | Needle carrier lock pawl | 1-5, 8 |
| 29 | Rear trackstop | 1, 3-5 |
| 30 | Needle cavity | 1-6, 6A, 7-9, 9A |
| 31 | Bending section | 1-5, 8 |
| 32 | Retaining surface | 1, 3-5, 8 |
| 33 | Tab relief slot | 1-5, 8 |
| 34 | Needle tip guard | 1-3, 6A, 8-9, 9A |
| 35 | Catheter retaining surface | 1-3, 5, 8 |
| 36 | Flashback vent | 6A |
| 37 | Needle aperture | 6A, 9A |
| 38 | Sealing surface | 6A, 9A, 12A, 14A |
| 39 | Cap retainer hub | 6A, 9 |
| 40 | Luer connector cavity | 6A, 9A |
| 41 | Valve face | 6A, 9A |
| 42 | Two-way valve | 12 |
| 43 | Standard male luer connector | 13-14, 14A |
| 44 | Vertical luer connector | 12, 14A, 15 |
| 45 | Flow path | 14A |
| 46 | Valve actuator | 12A |
| 47 | Luer body | 14A |
| 48 | Catheter applicator | 1-6, 6A, 8-9, 9A, 11-12, 13-14, 15 |
| 49 | Catheter appliance | 1-6, 6A, 8-9, 9A, 11-12, 13-14, 15 |
| 50 | Needle carrier module | 1-6, 6A, 8-9, 9A, 11-12, 13-14, 15 |

The invention claimed is:

1. A catheter and insertion device comprising:
   (a) a catheter applicator having a catheter for insertion into the vein of a patient, said catheter applicator comprising a paddle having a track down the center with a catheter retainer pawl at one end, a needle cavity at the opposite end and a rear track stop near the needle cavity end of said track;
   (b) a catheter appliance releasably secured to said catheter applicator said catheter appliance comprising
      (i) a catheter carrier body having an attachment surface in the form of a catheter flap,
      (ii) a catheter mounted on said catheter carrier body,
      (iii) a paddle retainer securing said catheter appliance to said catheter applicator, and
      (iv) a luer connector rotatably mounted on said catheter carrier body and in fluid communication with said catheter; and
   (c) a needle carrier module slidably mounted on said catheter applicator, said needle carrier having a hypodermic needle extending through said catheter.

2. The catheter and insertion device according to claim 1 further comprising a one-way check valve between said catheter and said luer connector.

3. The catheter and insertion device according to claim 1 further comprising a needle carrier having a flashback cavity containing a flashback indicator, a hypodermic needle mounted on said needle carrier to extend through said catheter and in fluid communication with said flashback cavity, a track follower and a needle carrier retainer spring, said needle carrier being mounted on said catheter applicator by said track follower.

4. A catheter and insertion device comprising:
   (a) a catheter applicator comprising a paddle having a track down the center with a catheter retainer pawl at one end, a needle cavity at the opposite end and a rear track stop near the needle cavity end of said track;
   (b) a catheter appliance releasably secured to said catheter applicator comprising a catheter carrier body having an attachment surface in the form of a catheter flap, a catheter mounted on said catheter carrier body, a paddle retainer securing said catheter appliance to said catheter applicator and a luer connector rotatably mounted on said body and in fluid communication with said catheter; and
   (c) a needle carrier module slidably mounted on said catheter applicator by a track follower and needle carrier retainer spring and comprising a needle carrier having a flashback cavity containing a flashback indicator, a hypodermic needle mounted on said needle carrier to extend through said catheter and in fluid communication with said flashback cavity and a track follower slidably secured on said track by a needle carrier.

5. The catheter and insertion device according to claim 4 further comprising a one-way check valve between said catheter and said luer connector.

* * * * *